United States Patent [19]

Kilpper et al.

[11] 4,276,433
[45] Jun. 30, 1981

[54] CONTINUOUS PREPARATION OF ANTHRANILIC ACID

[75] Inventors: Gerhard Kilpper, Battenberg; Johannes Grimmer, Ludwigshafen, both of Fed. Rep. of Germany

[73] Assignee: BASF Aktiengesellschaft, Fed. Rep. of Germany

[21] Appl. No.: 2,333

[22] Filed: Jan. 10, 1979

[51] Int. Cl.$^3$ .................................. C07C 101/54
[52] U.S. Cl. ........................................... 562/458
[58] Field of Search ............................... 562/458

[56] References Cited

U.S. PATENT DOCUMENTS

| | | | |
|---|---|---|---|
| 1,322,052 | 11/1919 | Potter | 562/458 |
| 2,653,971 | 9/1953 | Balch et al. | 562/458 |
| 3,322,820 | 5/1967 | Lehmann et al. | 562/458 |
| 3,847,974 | 11/1974 | Sturm et al. | 562/458 |
| 4,082,749 | 4/1978 | Quadbeck-Seeger et al. | 544/336 |

FOREIGN PATENT DOCUMENTS

| | | | |
|---|---|---|---|
| 1950281 | 4/1971 | Fed. Rep. of Germany | 562/458 |
| 2000698 | 2/1972 | Fed. Rep. of Germany | 562/458 |
| 2328757 | 1/1975 | Fed. Rep. of Germany | 562/458 |
| 2357749 | 5/1975 | Fed. Rep. of Germany | 562/458 |
| 1316332 | 5/1973 | United Kingdom | 562/458 |

OTHER PUBLICATIONS

Zabicky, The Chemistry of Amides, Interscience Publishers, N.Y., pp. 816-847, 1970.

*Primary Examiner*—G. T. Breitenstein
*Attorney, Agent, or Firm*—Keil & Witherspoon

[57] ABSTRACT

A process for the continuous preparation of anthranilic acid by a two-stage reaction of an alkali metal phthalamate and/or an alkali metal phthalimidate with an alkali metal hypohalite, the first stage being carried out substantially adiabatically and both stages being carried out at high flow rates and different temperatures, wherein first the phthalimide and/or phthalamic acid is dissolved in a defined excess amount of alkali metal hydroxide solution and the solution is only then mixed, and reacted, with the hypohalite, without further addition of excess alkali. The products are starting materials for the preparation of dyes and scents.

14 Claims, No Drawings

CONTINUOUS PREPARATION OF ANTHRANILIC ACID

The present invention relates to a process for the continuous preparation of anthranilic acid by a two-stage reaction of an alkali metal phthalamate and/or an alkali metal phthalimidate with an alkali metal hypohalte, the first stage being carried out substantially adiabatically and both stages being carried out at high flow rates and different temperatures, wherein first the phthalimide and/or phthalamic acid is dissolved in a defined excess amount of alkali metal hydroxide solution and the solution is only then mixed, and reacted, with the hypohalite, without further addition of excess alkali.

German Pat. No. 1,224,748 discloses a continuous conversion of an alkali metal phthalamate to anthranilic acid by oxidation with an alkali metal hypochlorite. The starting materials, in the form of their cooled aqueous solutions, are mixed with one another in a cooled mixing chamber and reacted in the first reaction stage, namely the formation of phenylisocyanate-2-carboxylic acid, in the part of a reaction column which contains a cooling system. In the second stage, namely the formation of anthranilic acid, the reaction temperature should not exceed 70° C. The description draws attention to the importance of removing the heat of reaction by cooling, especially in the first stage, and mentions a maximum temperature of +10° C. for the formation of the phenylisocyanate-2-carboxylic acid. The prior art also attaches importance to good cooling in batchwise methods of carrying out the reaction.

German Published Applications DAS Nos. 1,950,281 and DAS 2,000,698 disclose a process for the continuous preparation of anthranilic acid by reaction of an alkali metal phthalamate and/or an alkali metal phthalimidate with a hypohalite in an aqueous medium, wherein (a) an aqueous solution of an alkali metal phthalamate and/or an alkali metal phthalimidate and an aqueous solution of an alkali metal hypochlorite are mixed in a mixing apparatus, (b) the resulting mixture is reacted in the first part of narrow reaction tube at a high flow rate, at from 10° to 50° C., under substantially adiabatic conditions, hereafter (c) the reaction mixture which leaves the first part of the reaction tube at a high flow rate is allowed to complete the reaction in the second part of the said tube at from 60° to 80° C. and (d) anthranilic acid and/or isatoic anhydride are isolated in the conventional manner from the alkaline reaction mixture which leaves the tube, reducing agent being added, if appropriate, during stage (b) and/or stage (c).

In this process, only a part of the free alkali metal hydroxide is used at the stage of dissolving the starting material, whilst a further part is added to the hypochlorite solution. It is advantageous to use aqueous solutions containing from 10 to 50 percent by weight of phthalimide and/or phthalamic acid, the solutions containing from 1 to 1.1 moles of alkali metal hydroxide per mole of phthalimide or phthalamic acid. It is stated that the aqueous hypohalite solutions advantageously contain from 8 to 15 percent by weight of hypohalite and from 1 to 3, preferably from 0.02 to 2.1, moles of alkali metal hydroxide per mole of phthalimide or phthalamic acid.

In Example 1 (preparation of anthranilic acid) alkali metal hydroxide is present both in the phthalimide solution, in an amount of 1.1 moles of NaOH per mole of phthalimide, and in the hypochlorite solution (1.4 moles of NaOH per mole of phthalimide). German Published Application DAS No. 1,950,281 states that the formation of the end product is influenced by varying the alkali concentration in the starting solutions. Using from 0.9 to 1.1 moles of alkali per mole of phthalimide or phthalamic acid in the starting mixture gives isatoic anhydride. Only in that case does the above DAS—as shown in Example 2—provide that the entire amount of alkali is added to the starting material.

German Laid-Open Application DOS No. 2,328,757 describes a process for the preparation of amines, also including, for example, anthranilic acid, by reacting a carboxylic acid amide with a hypochlorite in the presence of bromine, iodine and/or a haloamide and excess alkali metal hydroxide. It is stated that it is advantageous to use aqueous suspensions containing from 1 to 50 percent by weight of the starting carboxylic acid amide. The aqueous hypochlorite solution in general contains from 5 to 15, preferably from 12 to 14, percent by weight of hypochlorite and may in addition contain from 0.2 to 2.5 moles, preferably from 1 to 2.1 moles, of alkali metal hydroxide per mole of hypochlorite. The initial mixture of the two starting materials may in general contain a total of from 0.2 to 2.5 moles, preferably from 1 to 2.1 moles, of alkali metal hydroxide (not counting the alkali contained in the hypochlorite) per mole of starting carboxylic acid amide, ie. per carboxylic acid amide group in the molecule. If the aqueous hypochlorite solution does not contain any free alkali metal hydroxide, it is advantageous to introduce from 0.2 to 2, preferably from 1 to 2, moles of alkali metal hydroxide per mole of hypochlorite at the start of, or in the course of, the reaction. The DOS states that to bring about the reaction an aqueous solution of the hypohalite is introduced into a mixture of the carboxylic acid amide starting material, the catalyst and water, and the batch is kept at the reaction temperature for from 1 to 4,000 seconds. Thereafter, in the case of phthalamic acid, aqueous alkali metal hydroxide solution is introduced and the mixture is kept for from one second to 3 hours at the reaction temperature, if necessary with heating. The higher the selected reaction temperature, the shorter, advantageously, is the reaction time before adding the alkali metal hydroxide solution. In a preferred embodiment, the carboxylic acid amide starting material, eg. phthalamic acid, is first prepared from the carboxylic acid anhydride and ammonia, with or without alkali metal hydroxide, at, in general, from 20° to 80° C., and the reaction mixture thus formed is employed directly, without isolating the reaction product, as the starting material for the process according to the invention. In Example 1, a phthalamic acid salt is first prepared in this way, there being no excess of sodium hydroxide over phthalamic acid in the solution, the solution is then mixed with a hypochlorite solution which does not contain any excess alkali metal hydroxide, and finally 2 moles of sodium hydroxide are added per mole of phthalamic acid.

A further process, described in German Laid-Open Application DOS No. 2,357,749, shows the corresponding preparation of amines by reacting carboxylic acid amides with hypochlorites in the presence of excess alkali metal hydroxide and of polymerization inhibitors. Advantageously, an aqueous suspension containing from 1 to 50 percent by weight of the carboxylic acid amide starting material is used. Here again, the aqueous hypochlorite solutions in general contain from 5 to 15, preferably from 12 to 14, percent by weight of hypochlorite and may in addition contain from 0.2 to 2.5 moles, preferably from 1 to 2.1 moles, of alkali metal hydroxide per mole of hypochlorite. The starting mixture of the two starting materials can in general contain a total of from 0.2 to 2.5 moles, preferably from 1 to 2.1 moles, of alkali metal hydroxide (not counting the alkali contained in the hypochlorite) per mole of carboxylic acid amide starting material, ie. per carboxylic acid amide group in the molecule. If the aqueous hypochlorite solution does not contain any free alkali metal hydroxide, it is advantageous to add from 0.2 to 2, preferably from 1 to 2, moles of alkali metal hydroxide per mole of hypochlorite at the start of, or in the course of, the reaction. The procedure in respect of addition of alkali metal hydroxide solution corresponds to that of German Laid-Open Application DOS No. 2,328,757, as is shown by all the Examples. Both the German Laid-Open Applications expressly state that only in the case of other carboxylic acid amides, but not in the case of phthalamic acid, is it advantageous to combine the alkali with the starting mixture from the very start and to carry out the reaction for from one second to 3 hours.

We have found that anthranilic acid can be prepared advantageously by the reaction of an alkali metal phthalamate and/or phthalimidate with a hypohalite in an aqueous medium, if (a) phthalimide and/or phthalamic acid is dissolved in an aqueous alkali metal hydroxide solution in a ratio of from 3 to 3.5 moles of alkali metal hydroxide per mole of phthalimide and/or of from 2 to 2.5 moles of alkali metal hydroxide per mole of phthalamic acid, (b) the resulting aqueous solution of alkali metal phthalamate and/or phthalimidate is mixed with an aqueous solution of an alkali metal hypochlorite in a mixing apparatus, (c) the resulting mixture is reacted in the first part of a reaction tube at a high flow rate, at from 10° to 54° C., under substantially adiabatic conditions, thereafter (d) the reaction mixture which leaves the first part of the reaction tube at a high flow rate is allowed to complete the reaction in the second part of the said tube at from 55° to 90° C. and (e) anthranilic acid is isolated in the conventional manner from the alkaline reaction mixture which leaves the tube.

Further, we have found that the process may be carried out advantageously by adding a reducing agent to the reaction mixture during stage (c) or (d).

Yet further, we have found that the process may be carried out advantageously if the reaction is carried out in the presence of bromine, iodine and/or an amide of the formula $$X-\overset{\overset{R^1}{|}}{N}-R^2 \qquad I$$

where $R^1$ is a sulfonic acid group, a sulfonate radical or a sulfonamide group, $R^2$ is a hydrogen atom, an aliphatic radical, chlorine or bromine, X is chlorine, bromine or hydrogen, and $R^1$ and $R^2$ may also, together with the adjacent nitrogen, form a heterocyclic radical which contains at least one sulfone group, or phosphonyl group of the formula

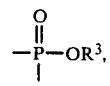

where $R^3$ is hydrogen or an alkali metal, adjacent to the nitrogen, and $R^1$ and $R^2$ may also together be

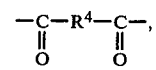

where $R^4$ is alkylene,

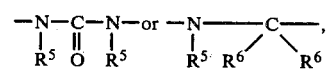

$R^5$ is hydrogen, chlorine or bromine and $R^6$ is an aliphatic radical.

Where sodium hydroxide and sodium hypochlorite are used, the reaction can be represented by the following equations:

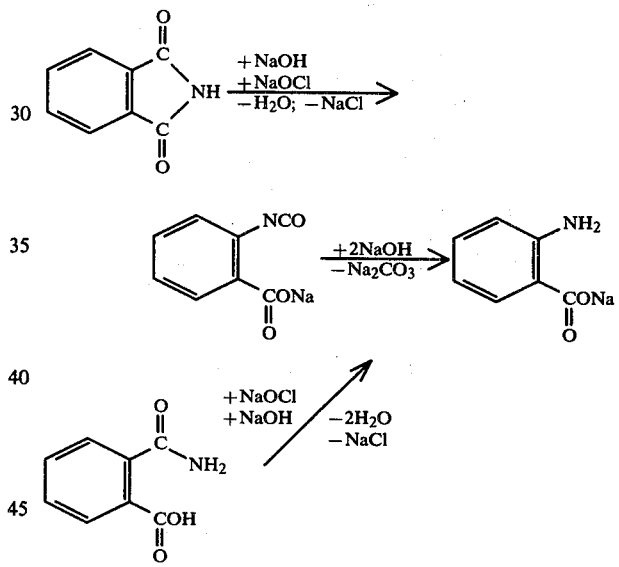

Compared to the conventional processes, the process according to the invention gives anthranilic acid more simply and more economically, in some cases in better yield and higher purity, and with substantially better space-time yield. The reaction takes place more rapidly and can thus be carried out in substantially smaller tubular reactors. The end product is obtained as coarser and better-developed crystals of lower residual moisture content. Less smeary crystals are obtained, which can be filtered and dried more easily, and which permit more rapid and trouble-free operation in the subsequent transport of solids in the drying installation. Furthermore, it is advantageous to add the entire excess alkali metal hydroxide solution in stage (a). In the conventional processes, the alkali metal hydroxide solution required for the chemical process to take place is added only in part to the phthalimide or phthalamic acid solution and in part to the alkali metal hypochlorite solution or is only subsequently added to the total mixture. In operation, fluctuations in the regulating system cause inaccuracies in the metering of the alkali metal hydroxide solution, which, in the conventional processes, have an adverse effect on the course of the process; for example, if insufficient sodium hydroxide solution is present in the phthalimide solution, there is the danger that the phthalimide will remain undissolved and cause blockages. Fluctuations in the amount of sodium hydroxide in the alkali metal hypochlorite solution lead to concentration changes which have an effect on the yield. The additional metering of alkali metal hydroxide solution into the total mixture of the starting materials (phthalimide or phthalamic acid and hypochlorite) further increases the number of regulating systems required. Accordingly, the operation of the process according to the invention is, by comparison, more reliable and requires fewer operatives and supervisors. The total operating time, including the preparation of the aqueous starting mixture and the working up of the reaction mixture, is shorter in the process according to the invention. All these advantageous results are surprising in the light of the prior art.

In stage (a), the starting material is dissolved in an aqueous alkali metal hydroxide solution, advantageously potassium hydroxide solution and especially sodium hydroxide solution. It is advantageous to use an aqueous solution containing from 10 to 50, preferably from 15 to 30, percent by weight (based on the amount of pure water) of phthalimide and/or phthalamic acid, which solution contains from 3 to 3.5, preferably from 3.1 to 3.2, moles of alkali metal hydroxide per mole of phthalimide and/or from 2 to 2.5, preferably from 2.1 to 2.2, moles of alkali metal hydroxide per mole of phthalamic acid. The solution is advantageously prepared continuously at from −5° to +50° C., preferably from 20° to 30° C., under atmospheric pressure or superatmospheric pressure. If a catalyst is used, for example one of the catalysts described in German Laid-Open Application DOS. No. 2,357,749 or, advantageously, one of those described in German Laid-Open Application DOS No. 2,328,757, the catalyst is advantageously already added to the starting material, or to its solution, in stage (a). However, it is also possible to add the catalyst, advantageously mixed with water, to the starting mixture either separately or together with the hypohalite.

Advantageous catalysts are bromine, iodine and/or the above amides I, in general in an amount of from 0.0001 to 0.1, preferably from 0.001 to 0.01, mole of catalyst per mole of phthalimide or phthalamic acid. Instead of the said materials, it is also possible to use compounds which form such materials under the reaction conditions, for example to use bromides and iodides instead of bromine and iodine respectively. Advantageously, water-soluble halides are used. These are, advantageously, the alkaline earth metal salts and especially the alkali metal salts, for example calcium bromide, calcium iodide, magnesium bromide, magnesium iodide, lithium bromide, lithium iodide and especially sodium bromide and iodide and potassium bromide and iodide. Preferred amides I are those where $R^1$ is a sulfonic acid group, a sulfonate radical, especially an alkali metal sulfonate radical, eg. a sodium sulfonate or potassium sulfonate radical, or a sulfonamide group, $R^2$ is chlorine, bromine, alkyl of 1 to 4 carbon atoms or, in particular, hydrogen, X is bromine, chlorine or, advantageously, hydrogen, $R^1$ and $R^2$ may also, together with the adjacent nitrogen, form a heterocyclic 5-membered or 6-membered ring which contains at least one sulfone group, or phosphonyl group of the formula

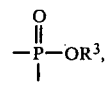

where $R^3$ is hydrogen or an alkali metal, such as sodium or potassium, adjacent to the nitrogen, and $R^1$ and $R^2$ may also together be

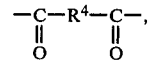

where $R^4$ is alkylene of 2 to 4 carbon atoms,

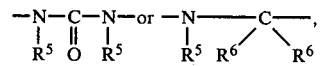

$R^5$ is hydrogen, chlorine or bromine and $R^6$ is alkyl of 1 to 4 carbon atoms, and especially methyl. A phenyl nucleus may also be fused to the above heterocyclic ring. Advantageously, the heterocyclic radical contains two sulfone or phosphonyl groups adjacent to the nitrogen, or two or three sulfonamido or phosphonamido groups, these groups in particular being present in one and the same ring in the case of polynuclear heterocyclic radicals. The above preferred radicals may in addition be substituted by groups or atoms which are inert under the reaction conditions, for example chlorine, bromine or alkyl of 1 to 4 carbon atoms, or carboxyl or carboxylate groups present as substituents of the phenyl nucleus.

Examples of suitable catalysts are glutarimide, adipamide and succinimide, and, preferably, cyanuric acid, 5,5-dimethylhydantoin, trisulfamide, N-methyl-sulfamic acid and sodium triimidometaphosphate, and corresponding mixtures of the above amides I; sulfamic acid and its salts, advantageously, alkali metal salts such as the sodium salt or potassium salt, and in particular sulfamide are particularly preferred, and may or may not be used as mixtures with the above amides I.

The aqueous hypochlorite solution of stage (b) advantageously contains from 5 to 15, especially from 12 to 14, percent by weight of hypochlorite and no substantial amounts—at most up to 0.01 mole—of excess alkali metal hydroxide per mole of phthalimide/phthalamic acid. Preferred alkali metal hypochlorites are the potassium salt and especially sodium hypochlorite. In general, the reaction is carried out using a ratio of from 1 to 2, preferably from 1 to 1.2, moles of hypohalite per mole of phthalimide and/or phthalamic acid. Advantageously, the starting material, in the form of its aqueous alkaline solution of the above concentration, obtained from stage (a), is mixed in the above ratio with the alkali metal hypochlorite solution in stage (b), in a mixing apparatus. This apparatus may be a mixing cell, mixing jet or chamber equipped with a high-speed stirrer. Mixing is as a rule effected continuously at from 0° to 50° C., advantageously from 25° to 45° C., under atmospheric or superatmospheric pressure.

The reaction is advantageously carried out in 2 reaction spaces (stages (c) and (d)), under conditions which substantially avoid back-mixing in both spaces, and under substantially adiabatic conditions in the first stage. The reaction takes place in 2 steps, namely reaction stage (c), the conversion of the starting material to the alkali metal phenylisocyanate-2-carboxylate via the alkali metal N-chloro-phthalamate, and the subsequent stage (d), namely the conversion of the alkali metal salt to anthranilic acid. The first reaction stage is carried out under substantially adiabatic conditions; as a rule, the heat of reaction which is liberated heats the reaction mixture to 20°–50° C. From the mixing apparatus, the reaction mixture passes into the reaction space for the first reaction stage (stage (c)) which consists of a reaction tube, which advantageously is narrow, and from there, after reaction, the mixture passes into the reaction space of the next stage (stage (d)). The mixing apparatus, the reaction space for the first stage and the solutions of the starting materials do not require cooling. A preferred feature of the process according to the invention is that back-mixing in stage (c) is substantially avoided, and that the reaction mixture is rapidly withdrawn from (c) and fed to stage (d), whilst substantially avoiding any back-mixing. Advantageously, the reaction mixture is caused to travel at a high flow rate by using a narrow cross-section of the reaction tube in the first stage and by using appropriate conveying pumps. Examples of pumps which may be used are jet pumps, rotary pumps, rotary piston pumps, Roots pumps, screw pumps, eccentric pumps, vane pumps, centrifugal pumps, axial pumps and propeller pumps. In a preferred embodiment of the process, the flow rates are determined by the cross-section and length of the reaction tube. For example, it is advantageous to use reactor cross-sections of from 10 to 10,000 $mm^2$ and flow rates of from 0.1 to 10, especially from 0.2 to 3, m/sec, preferably from 0.5 to 1 m/sec. At these flow rates, the starting material is as a rule substantially converted, in stage (c), to the alkali metal phenylisocyanate-2-carboxylate, via the nitrogen-chlorinated phthalamic acid, in a residence time of from 0.4 to 40, preferably from 0.7 to 20, seconds. As a result of the high flow rate, the alkali metal salt formed is immediately withdrawn from the reaction space of stage (c), fed to the next stage and there converted to anthranilic acid, in general with a residence time of from 0.3 to 150, preferably from 0.4 to 40, seconds. The high flow rate at the same time substantially prevents back-mixing over the entire conversion of the reaction mixture. In particular, back-mixing of the end product with the reaction mixture of stage (c) is avoided, hence suppressing the formation of by-products by reaction of the hypohalite or of the N-chlorinated phthalamic acid with the end product and/or by similar reactions in the mixtures of stages (c) and (d). The reaction in stage (c) is carried out at from 10° to 54° C., preferably from 20° to 54° C., especially from 20° to 45° C. and in stage (d) at from 55° to 90° C., preferably from 60° to 85° C., under atmospheric pressure or superatmospheric pressure. At the end of the reaction sequence, the reaction mixture is taken off and can be processed further as an alkaline solution of anthranilic acid, since the end product is produced in excellent purity. The end product can be isolated from the alkaline solution by precipitation with an acid, eg. hydrochloric acid or sulfuric acid, followed by filtration.

In stage (c), and especially in stage (d), the reaction can advantageously be carried out in the presence of a large variety of reducing agents, described in German Published Application DAS No. 2,000,698, which are soluble in, or miscible with, water and/or alkalis. Examples of suitable reducing agents are hydrides, eg. sodium borohydride and lithium triethoxy-aluminum hydride, reducing sulfur compounds, eg, sodium sulfide, sodium bisulfide, ammonium sulfide, sulfurous acid, sulfur dioxide, sodium dithionite, sodium thiosulfate, sodium formaldehyde-sulfoxylate and thiourea dioxide, hydrazine and its salts, eg. the sulfate or chloride, and glucose. The preferred reducing agents are sodium sulfite and sodium bisulfite. The reducing agents can be used in the stoichiometric ratio or in excess over the added hypohalite, preferably an excess of from 0.005 to 0.1 equivalent of reducing agent per mole of hypochlorite. It is advantageous to use an aqueous solution of the reducing agent, for example an aqueous sodium bisulfite solution of from 10 to 40 percent strength by weight.

The reducing agent can be added batchwise or, as a rule, continuously and is advantageously added to the reaction mixture after the reaction space of stage (c) and before the end of stage (d) of the reaction. It may be added to the mixture at several points or, advantageously, at a single point, during the conversion of the phenylisocyanate-2-carboxylic acid, formed in the first reaction stage, to anthranilic acid, and is advantageously added directly after completion of the conversion of the starting material to phenylisocyanate-2-carboxylic acid. As a rule, the completion of reaction stage (c) manifests itself by a temperature rise from 20°–30° C. to about 45°–50° C. The rate of addition as a rule depends on the flow rate of the reaction mixture but it is necessary to take account of the concentration of the solution added and of the above ratio of reducing agent to starting hypohalite. The reducing solution may be introduced in any desired manner, for example via a chamber equipped with a stirrer, via a mixing nozzle or, preferably, via a mixing cell. After addition of the reducing agent, the reaction can be carried out in the reaction tube at a high flow rate, for example at from 0.2 to 3 m/sec, or—without reducing the yield—in a reaction tube of any desired dimensions. The cross-section, flow rate and temperature of the starting solutions in general decide the length of the tube zone in which the first reaction stage (c) is carried out. For example, with a tube cross-section of 2,200 $mm^2$, a flow rate of about 1 m/sec and a starting temperature of about 40° C., stage (c) is as a rule complete after about 1.5 meters length of the reaction tube, after which the reducing agent is advantageously introduced.

The compounds which may be prepared by the process according to the invention are valuable starting materials for the preparation of dyes and scents. Regarding their use, reference may be made to the patents mentioned and to Ullmanns Encyklopädie der technischen Chemie (4th edition), volume 8, page 375.

In the Examples which follow, parts are by weight and bear the same relation to parts by volume as that of the kilogram to the liter.

EXAMPLE 1

The installation used comprises a mixing nozzle and a reaction tube having a length of 1.1 meters and an internal diameter of 53 millimeters. Per hour, 590 parts of liquid phthalimide are continuously dissolved, in a mixing nozzle, in 2,103 parts of aqueous 25 percent strength by weight sodium hydroxide solution and 4,752 parts of water and mixed continuously with 18 parts per hour of a 30 percent strength by weight aqueous solution of sodium amidosulfonate. The resulting solution is mixed, in the mixing nozzle, with 1,750 parts per hour of an aqueous sodium hypochlorite solution (242 parts of sodium hypochlorite; 13.8 percent by weight of active chlorine) at 42° C. The flow rate in the downstream reaction tube is 1.07 meters per second. The residence time is one second. The mixture is reacted substantially adiabatically (temperature rising from 42° to 53° C.) in the first part, 0.3 m long, of the reaction tube (stage c), whilst in the remainder of the reaction space the exothermic effect raises the mixture to 89° C. The mixture is mixed continuously with 25 parts per hour of 40 percent strength by weight aqueous sodium bisulfite solution and is then cooled to 10° C. and brought to pH 4.2 with hydrochloric acid, the product is filtered off and the filter residue is washed with water and dried. 535 Parts per hour (97% of theory) of 99.3% pure anthranilic acid, of melting point 146.2° C., are obtained; the space-time yield is 268 parts per hour per liter.

EXAMPLE 2

If the reaction is carried out as described in Example 1, but without addition of amidosulfonic acid, 506 parts per hour (92% of theory) of anthranilic acid of 99.1 percent purity, melting at 146.1° C., are obtained. The space-time yield is 27 parts per hour per liter.

COMPARISON

|  | Amount filtered off (parts of anthranilic acid/h . m²) | Residual moisture content (% by weight after filtering but before drying) |
| --- | --- | --- |
| Example 1 | 150 | 6 |
| Example 2 | 130 | 9 |
| Example 1 of DAS 1,950,281 | 90 | 20 |
| Example of DAS 2,000,698 | 90 | 20 |
| Example 1 of DOS 2,328,757 | 120 | 10 |

We claim:

1. A process for the continuous preparation of anthranilic acid by reaction of an alkali metal phthalamate and/or alkali metal phthalimidate with a hypohalite in an aqueous medium, wherein the reaction is carried out in the presence of a catalytic amount of bromine, iodine and/or amide of the formula

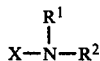

wherein $R^1$ is a sulfonic acid group, a sulfonate radical or a sulfonamide group, $R^2$ is a hydrogen atom, an aliphatic radical, chlorine or bromine, X is chlorine, bromine or hydrogen, and $R^1$ and $R^2$ may also, together with the adjacent nitrogen, be members of a heterocyclic radical which contains at least one sulfone group or phosphonyl group of formula

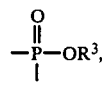

where $R_3$ is hydrogen or an alkali metal, adjacent to the nitrogen and $R^1$ and $R^2$ may also together be

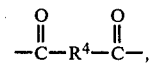

where $R^4$ is alkylene,

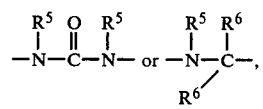

$R^5$ is hydrogen, chlorine or bromine and $R^6$ is an aliphatic radical, wherein (a) phthalimide and/or phthalamic acid is dissolved in an aqueous alkali metal hydroxide solution in a ratio of from 3 to 3.5 moles of alkali metal hydroxide per mole of phthalimide and/or of from 2 to 2.5 moles of alkali metal hydroxide per mole of phthalamic acid, (b) the resulting aqueous solution of alkali metal phthalamate and/or phthalimidate is mixed with an aqueous solution of an alkali metal hypochlorite in a mixing apparatus, (c) the resulting mixture is reacted in the first part of a reaction tube at a high flow rate, at from 10° to 54° C., under substantially adiabatic conditions, thereafter (d) the reaction mixture which leaves the first part of the reaction tube at a high flow rate is allowed to complete the reaction in the second part of the said tube at from 55° to 90° C. and (e) anthranilic acid is isolated in the conventional manner from the alkaline reaction mixture which leaves the tube.

2. A process as claimed in claim 1, wherein a reducing agent is added to the reaction mixture during stage (c) or (d).

3. A process as claimed in claim 1, wherein the reaction in stage (a) is carried out with an aqueous solution containing from 10 to 50 percent by weight (based on the amount of pure water) of phthalimide and/or phthalamic acid and from 3.1 to 3.2 moles of alkali metal hydroxide per mole of phthalimide and/or from 2.1 to 2.2 moles of alkali metal hydroxide per mole of phthalamic acid.

4. A process as claimed in claim 1, wherein the reaction in stage (a) is carried out at from −5° to +50° C.

5. A process as claimed in claim 1 or 2, wherein the reaction using bromine, iodine and/or an amide I is carried out with from 0.001 to 0.01 mole of catalyst per mole of phthalimide or phthalamic acid.

6. A process as claimed in claim 1, wherein the reaction is carried out with glutarimide, adipimide, succinimide, 5,5-dimethylhydantoin, trisulfamide, N-methylsulfamic acid, sodium triimidometaphosphate, sulfamic acid and its salts, or sulfamide.

7. A process as claimed in claim 1, wherein the reaction in stage (b) is carried out with an aqueous hypochlorite solution of from 5 to 15 percent strength by weight.

8. A process as claimed in claim 1, wherein the reaction in stage (b) is carried out using a ratio of from 1 to 2 moles of hypohalite per mole of phthalimide and/or phthalamic acid.

9. A process as claimed in claim 1, wherein the reaction is carried out in 2 reaction spaces in stage (c) and (d), whilst substantially avoiding back-mixing in both spaces, and under substantially adiabatic conditions.

10. A process as claimed in claim 1, wherein the reaction in stage (c) and (d) is carried out with a reactor cross-section of from 10 to 10,000 mm² and a flow rate of from 0.1 to 10 m/sec.

11. A process as claimed in claim 1, wherein the reaction is carried out with a residence time of from 0.4 to 40 seconds in stage (c) and with a residence time of from 0.3 to 150 seconds in stage (d).

12. A process as claimed in claim 1, wherein the reaction in stage (c) is carried out at from 20° to 54° C. and the reaction in stage (d) is carried out at from 60° to 85° C.

13. A process as claimed in claim 1, wherein the reaction in stage (c) or stage (d) is carried out with sodium borohydride, lithium triethoxy-aluminum hydride, sodium sulfide, sodium bisulfide, ammonium sulfide, sulfurous acid, sulfur dioxide, sodium dithionite, sodium thiosulfate, sodium formaldehyde-sulfoxylate, thiourea dioxide, hydrazine, its sulfate or chloride, glucose, sodium sulfite or sodium bisulfite.

14. A process as claimed in claim 1, wherein the reaction is carried out with from 0.005 to 0.1 equivalent of reducing agent per mole of hypochlorite.

* * * * *